United States Patent [19]

Försch et al.

[11] 4,395,409

[45] Jul. 26, 1983

[54] CARBAMOYLOXYAMINO-1,4-BEN-ZODIAZEPINES AND MEDICAMENTS CONTAINING THESE COMPOUNDS

[75] Inventors: Manfred Försch, Nauheim; Hermann Gerhards, Hofheim am Taunus, both of Fed. Rep. of Germany

[73] Assignee: Hoechst Aktiengesellschaft, Frankfurt am Main, Fed. Rep. of Germany

[21] Appl. No.: 269,689

[22] Filed: Jun. 2, 1981

[30] Foreign Application Priority Data

Jun. 4, 1980 [DE] Fed. Rep. of Germany ....... 3021107

[51] Int. Cl.³ .................. C07D 243/20; A61K 31/55
[52] U.S. Cl. .......................... 424/244; 260/239 BD; 260/239.3 D; 546/272; 424/263
[58] Field of Search ................. 260/239 BD, 239.3 D; 424/247, 244, 263; 546/272

[56] References Cited

U.S. PATENT DOCUMENTS

| | | | |
|---|---|---|---|
| 3,205,223 | 9/1965 | Bell ........................................ | 260/239 |
| 3,268,586 | 8/1966 | Berger et al. ................. | 260/239.3 D |
| 3,649,617 | 3/1972 | Hester .......................... | 260/239 BD |
| 3,678,036 | 7/1972 | Archer et al. ............... | 260/239.3 D |
| 3,799,920 | 3/1974 | Ferrari et al. ............... | 260/239.3 D |
| 3,825,533 | 7/1974 | Nudelman et al. .......... | 260/239.3 D |
| 3,896,109 | 7/1975 | Hester .......................... | 260/239.3 D |
| 4,235,897 | 11/1980 | Demarne et al. ............. | 260/239.3 D |
| 4,325,957 | 4/1982 | Zeugner et al. ..................... | 424/263 |

FOREIGN PATENT DOCUMENTS

| | | | |
|---|---|---|---|
| 476528 | 9/1975 | Australia ..................... | 260/239.3 D |
| 2504937 | 8/1975 | Fed. Rep. of Germany . | 260/239.3 D |

OTHER PUBLICATIONS

Hester and Rudzik, "Benzodiazepines", *J. Med. Chem.*, vol. 17, pp. 293–295, (1974).
Wagner and Zook, *Synthetic Organic Chemistry*, (1953), p. 645.

*Primary Examiner*—Nicholas S. Rizzo
*Assistant Examiner*—G. Hendricks
*Attorney, Agent, or Firm*—Curtis, Morris & Safford

[57] ABSTRACT

What are disclosed are 1,4-benzodiazepines, having a carbamoyloxyamino group, of the following formula I tautomers thereof of the following formula IA physiologically tolerated salts thereof, said compounds having an anxiolytic action without sedating, a process for the preparation of these new compounds, pharmaceutical agents which contain the active compounds, and methods for treating anxiety states with said compounds.

9 Claims, No Drawings

CARBAMOYLOXYAMINO-1,4-BENZODIAZE-PINES AND MEDICAMENTS CONTAINING THESE COMPOUNDS

The present invention relates to a new class of carbamoyloxyamino compounds which have an anxiolytic action without sedating, to a process for the preparation of these new compounds, and to pharmaceutical agents which contain the active compounds according to the invention and their use as medicaments for the treatment of anxiety states.

The object of the invention are 1,4-benzodiazepines having a carbamoyloxyamino grouping of the formula I

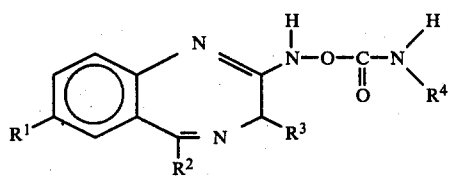

and the tautomeric compounds of the formula IA

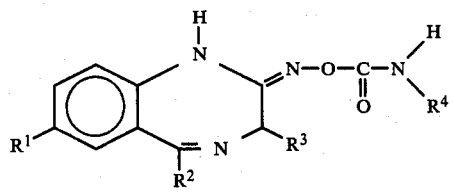

and the physiologically tolerated salts thereof, wherein $R^1$ is a halogen atom, or a nitro or trifluoromethyl group; $R^2$ is phenyl, pyridyl or a phenyl ring which is mono- or di-substituted by $C_1$-$C_4$-alkyl, $C_1$-$C_4$-alkoxy, hydroxy, halogen or trifluoromethyl; $R^3$ is hydrogen or $C_1$-$C_4$-alkyl, monoalkylcarbamoyloxy, or dialkylcarbamoyloxy, and $R^4$ is phenyl or a phenyl ring which is mono- or di-substituted by halogen, nitro, cyano, trifluoromethyl, $C_1$-$C_4$-alkyl or alkoxy, hydroxy or dialkylamino with 1 to 4 C-atoms in each alkyl group. In the foregoing definitions, halogen is in each case preferably fluorine, chlorine or bromine.

The compounds according to the invention, of the formulas I and IA, can be prepared (a) by reacting a compound of the formula II

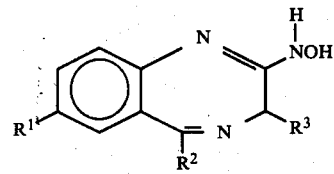

wherein $R^1$, $R^2$ and $R^3$ have the meaning given above, with an isocyanate of the formula III $$O=C=N-R^4 \quad (III)$$

or with a carbamic acid derivative of the formula IV which is capable of reaction,

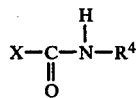

wherein X represents halogen or the phenoxy radical and $R^4$ has the meaning given above;

(b) by reacting a compound of the formula V

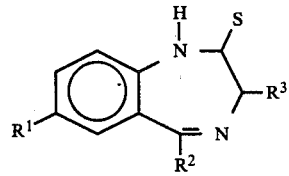

wherein $R^1$, $R^2$ and $R^3$ have the meaning given above, with hydroxylamine, or with a salt of hydroxylamine from which the base is liberated during the reaction, followed by reaction with an isocyanate of the formula III or a carbamic acid derivative of the formula IV; or (c) by reacting a compound of the formula V with an O-acylated hydroxylamine of the formula VI

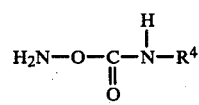

in which $R^4$ has the meaning given above.

The preparation of the compounds of formula I according to the invention by to process (a) from a compound of the general formula II and an isocyanate is carried out at a temperature of from 0° to 120° C., preferably at 20° to 80° C. in an inert aprotic solvent, preferably ether, such as dioxane, tetrahydrofuran, 1,2-dimethoxyethane, diethylene glycol dimethyl ether or dimethylformamide, dimethyl sulfoxide or hexamethylphosphoric acid triamide. After the reaction has ended, the reaction mixture is filtered off and the product is precipitated by addition of cold water to the reaction mixture. If necessary, the solvent is previously evaporated in vacuo and only then is water added to the reaction mixture. The crude product can be purified by recrystallization from a solvent. The reaction of compounds of the general formula II with carbamic acid halides of the formula IV is carried out in an inert solvent, preferably in toluene, dioxane, tetrahydrofuran, 1,2-dimethoxyethane, dimethylformamide, chloroform or methylene chloride. If appropriate, the addition of auxiliary bases, for example, alkali metal hydroxides, alkali metal alcoholates, heterocyclic nitrogen bases, such as pyridine, or tertiary amines, preferably triethylamine or ethyl diisopropylamine, is advantageous.

The reaction is carried out at $-10°$ to 60° C., preferably at 0° to room temperature.

The reaction of compounds of the formula II with phenyl carbamate is carried in alcohols, preferably in methanol. The reaction temperature is between room temperature and the boiling point of the particular solvent.

In process (b), a compound of the formula V is reacted with a hydroxylamine solution in an inert aprotic solvent, as indicated in process (a). If necessary, the hydroxylamine can be liberated in situ from a hydroxylamino acid addition salt by addition of acid-binding agents, such as, for example, alkali metal hydroxides, carbonates, bicarbonates or alkanolates, heterocyclic nitrogen bases, such as pyridine, or tertiary amines, preferably alkali metal bicarbonates, in particular sodium bicarbonate.

The reaction can be carried out at room temperature or at moderately elevated temperatures up to 60° C. The reaction time is 2 to 24 hours at room temperature, and the reaction mixture is preferably allowed to stand overnight at room temperature.

Before the addition of the isocyanate of the formula III, the reaction mixture is filtered off and worked up as described under process (a).

In process (c), the thio compound of the formula V is reacted with an O-acylated hydroxylamine of the formula VI in a solvent, preferably alcohol, methanol or isopropanol. The use of dimethylformamide, dioxane, tetrahydrofuran or diethylene glycol dimethyl ether can also be advantageous. This process is carried out, according to the substituent $R^4$, at $-10°$ C. to 60° C., preferably at 0° C. to room temperature.

The O-acylated hydroxylamines of the formula VI may be prepared from the corresponding O-acylated acethydroximic acid ethyl esters according to G. ZINNER and co-workers, Archiv der Pharmazie (Archive of Pharmacy), 303, page 317 (1970):

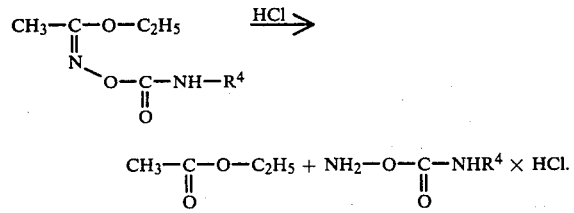

The O-acylated hydroxylamines of the formula VI are preferably employed in the form of their salts, in particular of their hydrochlorides. Alkali metal hydroxides, carbonates, bicarbonates or alcoholates, heterocyclic nitrogen bases such as pyridine, or tertiary amines, preferably alkali metal bicarbonates, in particular sodium bicarbonate, can be employed, for example, as acid-binding agents for reactions of these O-acylated hydroxylamines.

Although the synthesis of the starting materials of the formula II in which $R^3$ is a hydrogen atom is, in principle, described in German Offenlegungsschriften Nos. 2,005,176 and 2,135,595, and in U.S. Pat. Specification No. 3,857,854, it cannot, in part, be reproduced.

In these works, the compounds of the formula II are prepared from the thiolactams of the formula V by reaction with hydroxylammonium chloride and sodium bicarbonate in boiling methanol, with a reaction time of two hours. It has been established that, under these conditions, large amounts of by-products are produced, which can only be separated off by means of a troublesome purification by column chromatography. In addition to this, compounds of the general formula II have proved to be sensitive to acids.

A method has now been found as described in process (b). In this process, compounds of the formula V are reacted with hydroxylamine or a salt of this compound, preferably in dioxane/dimethylformamide, if necessary with the addition of sodium bicarbonate, and an isocyanate of the formula III is then added to the mixture. The compounds of the general formula II are not isolated in this process.

The preparation of the compounds of the formula II proceeds particularly smoothly if freshly crystallized hydroxylamine according to H. Lecher and J. Hofmann in Chem. Ber. 55, page 912 (1922) is employed in the reaction.

Those starting materials of the formula V which are not described in the literature [G. Archer and L. H. Sternbach, J. Org. Chem. 20, page 231 (1964); U.S. Pat. No. 3,422,091], are prepared by reaction of the known amides of the general formula VII, wherein $R^1$, $R^2$ and $R^3$ have the meanings mentioned under formula I,

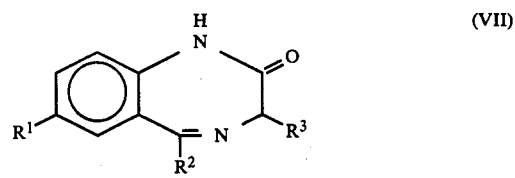

with phosphorus pentasulfide in pyridine at 100° C., or with dimeric p-methoxyphenylthionophosphine sulfide in dioxane according to S. O. Lawesson in Bull. Soc. Chim. Belg. 87, 229 (1978).

The invention also relates to those embodiments of the process in which a compound obtainable as an intermediate product at some stage of the process is used as the starting material and the additional steps of the process are carried out, or in which the process is interrupted at some stage, or in which a compound employed as the starting material is formed under the reaction conditions or is employed in the form of a reactive derivative or salt.

Apart from those mentioned in the examples, the following compounds according to the invention can be preferably prepared: 7-bromo-2-(3-chlorophenylcarbamoyloxyamino)-5-phenyl-3H-1,4-benzodiazepine, 7-bromo-2-(3-fluorophenylcarbamoyloxyamino)-5-phenyl-3H-1,4-benzodiazepine, 7-bromo-2-(3-bromophenylcarbamoyloxyamino)-5-phenyl-3H-1,4-benzodiazepine, 7-bromo-2-(3,4-dichlorophenylcarbamoyloxyamino)-5-phenyl-3H-1,4-benzodiazepine, 7-bromo-2-(2,6-dimethylphenylcarbamoyloxyamino)-5-phenyl-3H -1,4-benzodiazepine, 7-bromo-2-(3-trifluoromethylphenylcarbamoyloxyamino)-5-phenyl-3H-1,4-benzodiazepine, 7-bromo-2-(4-chlorophenylcarbamoyloxyamino)-5-phenyl-3H-1,4-benzodiazepine, 7-bromo-2-(3chlorophenylcarbamoyloxyamino)-5-(2-fluorophenyl)-3H-1,4-benzodiazepine, 7-bromo-2-(3-fluorophenylcarbamoyloxyamino)-5-(2-fluorophenyl)-3H-1,4-benzodiazepine, 7-bromo-2-(3-bromophenylcarbamoyloxyamino)-5-(2-fluorophenyl)-3H-1,4-benzodiazepine, 7-bromo-2-(3,4-dichlorophenylcarbamoyloxyamino)-5-(2-fluorophenyl)-3H-1,4-benzodiazepine, 7-bromo-2-(2,6-dimethylphenylcarbamoyloxyamino)-5-(2-fluorophenyl)-3H-1,4-benzodiazepine, 7-bromo-2-(3-trifluoromethylphenylcarbamoyloxyamino)-5-(2-fluorophenyl)-3H-1,4-benzodiazepine, 7-bromo-2-(4-chlorophenylcarbamoyloxyamino)-5-(2-fluorophenyl)-3H-1,4-benzodiazepine, 7-bromo-2-(3-chlorophenylcarbamoyloxyamino)-5-(2-chlorophenyl)-3H-1,4-benzodiazepine, 7-bromo-2-(3-fluorophenylcarbamoyloxyamino)-5-(2-chlorophenyl)-3H-1,4-benzodiazepine, 7-bromo-2-(3-bromophenylcarbamoyloxyamino)-5-(2-chlorophenyl)-3H-1,4-benzodiazepine, 7-bromo-2-(3,4-dichlorophenylcarbamoyloxyamino)-5-(2-chlorophenyl)-3H-1,4-benzodiazepine, 7-bromo-2-(2,6-dimethylphenylcarbamoyloxyamino)-5-(2-chlorophenyl)-3H-1,4-benzodiazepine, 7-bromo-2-(3-trifluoromethylphenylcarbamoyloxyamino)-5-(2-chlorophenyl)-3H-1,4-benzodiazepine, 7-bromo-2-(4-chlorophenylcarbamoyloxyamino)-5-(2-chlorophenyl)-3H-1,4-benzodiazepine, 7-bromo-2-(3-chlorophenylcarbamoyloxyamino)-5-(2-bromophenyl)-3H-1,4-benzodiazepine, 7-bromo-2-(3-fluorophenylcarbamoyloxyamino)-5-(2-bromophenyl)-3H-1,4-benzodiazepine, 7-bromo-2-(3-bromophenylcarbamoyloxyamino)-5-(2-bromophenyl)-3H-1,4-benzodiazepine, 7-bromo-2-(3,4-dichlorophenylcarbamoyloxyamino)-5-(2-bromophenyl)-3H-1,4-benzodiazepine, 7-bromo-2-(2,6-dimethylphenylcarbamoyloxyamino)-5-(2-bromophenyl)3H-1,4-benzodiazepine, 7-bromo-2-(3-trifluorophenylcarbamoyloxyamino)-5-(2-bromophenyl)-3H-1,4-benzodiazepine, 7-bromo-2-(4-chlorophenylcarbamoyloxyamino)-5-(2-bromophenyl)-3H-1,4-benzodiazepine, 7-bromo-2-(3-chlorophenylcarbamoyloxyamino)-5-(2-pyridyl)-3H-1,4-benzodiazepine, 7-bromo-2-(3-fluorophenylcarbamoyloxyamino)-5-(2-pyridyl)-3H-1,4-benzodiazepine, 7-bromo-2-(3-bromophenylcarbamoyloxyamino)-5-(2-pyridyl)-3H-1,4-benzodiazepine, 7-bromo-2-(3,4-dichlorophenylcarbamoyloxyamino)-5-(2-pyridyl)-3H-1,4-benzodiazepine, 7-bromo-2-(2,6-dimethylphenylcarbamoyloxyamino)-5-(2-pyridyl)-3H-1,4-benzodiazepine, 7-bromo-2-(3-trifluoromethylphenylcarbamoyloxyamino)-5-(2-pyridyl)-3H-1,4-benzodiazepine, 7-bromo-2-(4-chlorophenylcarbamoyloxyamino)-5-(2-pyridyl)-3H-1,4-benzodiazepine, 7-chloro-2-(3-chlorophenylcarbamoyloxyamino)-5-phenyl-3H-1,4-benzodiazepine, 7-chloro-2-(3-fluorophenylcarbamoyloxyamino)-5-phenyl-3H-1,4-benzodiazepine, 7-chloro-2-(3-bromophenylcarbamoyloxyamino)-5-phenyl-3H-1,4-benzodiazepine, 7-chloro-2-(3,4-dichlorophenylcarbamoyloxyamino)-5-phenyl-3H-1,4-benzodiazepine, 7-chloro-2-(2,6-dimethylphenylcarbamoyloxyamino)-5-phenyl 3H-1,4-benzodiazepine, 7-chloro-2-(3-trifluoromethylphenylcarbamoyloxyamino)-5-phenyl-3H-1,4-benzodiazepine, 7-chloro-2-(4-chlorophenylcarbamoyloxyamino)-5-phenyl-3H-1,4-benzodiazepine, 7-chloro-2-(3-chlorophenylcarbamoyloxyamino)-5-(2-fluorophenyl)-3H-1,4-benzodiazepine, 7-chloro-2-(3-fluorophenylcarbamoyloxyamino)-5-(2-fluorophenyl)-3H-1,4-benzodiazepine, 7-chloro-2-(3-bromophenylcarbamoyloxyamino)-5-(2-fluorophenyl)-3H-1,4-benzodiazepine, 7-chloro-2-(3,4-dichlorophenylcarbamoyloxyamino)-5-(2-fluorophenyl)-3H-1,4-benzodiazepine, 7-chloro-2-(2,6-dimethylphenylcarbamoyloxyamino)-5-(2-fluorophenyl)-3H-1,4-benzodiazepine, 7-chloro-2-(3-trifluorophenylcarbamoyloxyamino)-5-(2-fluorophenyl)-3H-1,4-benzodiazepine, 7-chloro-2-(4-chlorophenylcarbamoyloxyamino)-5-(2-fluorophenyl)-3H-1,4-benzodiazepine, 7-chloro-2-(3-chloro-4-methylphenylcarbamoyloxyamino)-5-(2-fluorophenyl)-3H-1,4-benzodiazepine, 7-chloro-2-(3-chlorophenylcarbamoyloxyamino)-5-(2-chlorophenyl)-3H-1,4-benzodiazepine, 7-chloro-2-(3-fluorophenylcarbamoyloxyamino)-5-(2-chlorophenyl)-3H-1,4-benzodiazepine, 7-chloro-2-(3-bromophenylcarbamoyloxyamino)-5-(2-chlorophenyl)-3H-1,4-benzodiazepine, 7-chloro-2-(3,4-dichlorophenylcarbamoyloxyamino)-5-(2-chlorophenyl)-3H-1,4-benzodiazepine, 7-chloro-2-(2,6-dimethylphenylcarbamoyloxyamino)-5-(2-chlorophenyl)-3H-1,4-benzodiazepine, 7-chloro-2-(3-trifluoromethylphenylcarbamoyloxyamino)-5-(2-chlorophenyl)-3H-1,4-benzodiazepine, 7-chloro-2-(4-chlorophenylcarbamoyloxyamino)-5-(2-chlorophenyl)-3H-1,4-benzodiazepine, 7-cyano-2-(3-chlorophenylcarbamoyloxyamino)-5-phenyl-3H-1,4-benzodiazepine, 7-cyano-2-(3-chlorophenylcarbamoyloxyamino)-5-(2-fluorophenyl)-3H-1,4-benzodiazepine, 7-cyano-2-(3-chlorophenylcarbamoyloxyamino)-5-(2-pyridyl)-3H-1,4-benzodiazepine, 7-cyano-2-(3-chlorophenylcarbamoyloxyamino)-5-(2-chlorophenyl)-3H-1,4-benzodiazepine, 7-chloro-2-(3-chlorophenylcarbamoyloxyamino)-5-(2-pyridyl)-3H-1,4-benzodiazepine, 7-chloro-2-(3-fluorophenylcarbamoyloxyamino)-5-(2-pyridyl)-3H-1,4-benzodiazepine, 7-chloro-2-(3-bromophenylcarbamoyloxyamino)-5-(2-pyridyl)-3H-1,4-benzodiazepine, 7-chloro-2-(3,4-dichlorophenylcarbamoyloxyamino)-5-(2-pyridyl)-3H-1,4-benzodiazepine, 7-chloro-2-(2,6-dimethylphenylcarbamoyloxyamino)-5-(2-pyridyl)-3H-1,4-benzodiazepine, 7-chloro-2-(3-trifluoromethylphenylcarbamoyloxyamino)-5-(2-pyridyl)-3H-1,4-benzodiazepine, 7-chloro-2-(4-chlorophenylcarbamoyloxyamino)-5-(2-pyridyl)-3H-1,4-benzodiazepine, 7-nitro-2-(3-chlorophenylcarbamoyloxyamino-3-hydroxy-5-(2-fluorophenyl)-3H-1,4-benzodiazepine, 7-bromo-2-(3-chlorophenylcarbamoyloxyamino)-3-hydroxy-5-(2-pyridyl)-3H-1,4-benzodiazepine, 7-bromo-2-phenylcarbamoyloxyamino-3-hydroxy-5-(2-pyridyl)-3H-1,4-benzodiazepine, 7-chloro-2-(3-chlorophenylcarbamoyloxyamino)-3-hydro-5-phenyl-3H-1,4-benzodiazepine, 7-chloro-2-phenylcarbamoyloxyamino-3-hydroxy-5-phenyl-3H-1,4-benzodiazepine, 7-chloro-2-(3-chlorophenylcarbamoyloxyamino)-3-hydroxy-5-(2-chlorophenyl)-3H-1,4-benzodiazepine, 7-chloro-2-phenylcarbamoyloxyamino-3-hydroxy-5-(2-chlorophenyl)-3H-1,4-benzodiazepine, 7-chloro-2-(3-chlorophenylcarbamoyloxyamino)-3-hydroxy-5-(2-fluorophenyl)-3H-1,4-benzodiazepine, 7-chloro-2-phenylcarbamoyloxyamino-3-hydroxy-5-(2-fluorophenyl)-3H-1,4-benzodiazepine, 7-nitro-2-(3-chlorophenylcarbamoyloxyamino)-3-hydroxy-5-(2-chlorophenyl)-3H-1,4-benzodiazepine, 7-nitro-2-phenylcarbamoyloxyamino-3-hydroxy-5-(2-fluorophenyl)-3H-1,4-benzodiazepine, 7-nitro-2-(3-chlorophenylcarbamoyloxyamino)-3-hydroxy-5-phenyl-3H-1,4-benzodiazepine, 7-nitro-2-phenylcarbamoyloxyamino-3-hydroxy-5-phenyl-3H-1,4-benzodiazepine, 7-nitro-2-phenylcarbamoyloxyamino-3-hydroxy-5-(2-chlorophenyl)-3H-1,4-benzodiazepine, 7-nitro-2-(3-chlorophenylcarbamoyloxyamino)-5-phenyl-3H-1,4-benzodiazepine, 7-nitro-2-(3-fluorophenylcarbamoyloxyamino)-5-phenyl-3H-1,4-benzodiazepine, 7-nitro-2-(3-bromophenylcarbamoyloxyamino)-5-phenyl-3H-1,4-benzodiazepine, 7-nitro-2-(3,4-dichlorophenylcarbamoyloxyamino)-5-phenyl-3H-1,4-benzodiazepine, 7-nitro-2-(2,6-dimethylphenylcarbamoyloxyamino)-5-phenyl-3H-1,4-benzodiazepine, 7-nitro-2-(3-trifluoromethylphenylcarbamoyloxyamino)-5-phenyl-3H-1,4-benzodiazepine, 7-nitro-2-(4-chlorophenylcarbamoyloxyamino)-5-phenyl-3H-1,4-benzodiazepine, 7-nitro-2-(3-chlorophenylcarbamoyloxyamino)-5-(2-chlorophenyl)-3H-1,4-benzodiazepine, 7-nitro-2-(3-fluorophenylcarbamoyloxyamino)-5-(2-chlorophenyl)-3H-1,4-benzodiazepine, 7-nitro-2-(3-bromophenylcarbamoyloxyamino)-5-(2-chlorophenyl)-3H-1,4-benzodiazepine, 7-nitro-2-(3,4-dichlorophenylcarbamoyloxyamino)-5-(2-chlorophenyl)-3H-1,4-benzodiazepine, 7-nitro-2-(2,6-dimethylphenylcarbamoyloxyamino)-5-(2-chlorophenyl)-3H-1,4-benzodiazepine, 7-nitro-2-(3-trifluoromethylphenylcarbamoyloxyamino)-5-(2-chlorophenyl)-3H-1,4-benzodiazepine, 7-nitro-2-(4-chlorophenylcarbamoyloxyamino)-5-(2-chlorophenyl)-3H-1,4-benzodiazepine, 7-nitro-2-(3-chloro-4-methylphenylcarbamoyloxyamino)-5-(2-chlorophenyl)-3H-1,4-benzodiazepine, 7-nitro-2-(3-chlorophenylcarbamoyloxyamino)-5-(2-fluorophenyl)-3H-1,4-benzodiazepine, 7-nitro-2-(3-fluorophenylcarbamoyloxyamino)-5-(2-fluorophenyl)-3H-1,4-benzodiazepine, 7-nitro-2-(3-bromophenylcarbamoyloxyamino)-5-(2-fluorophenyl)-3H-1,4-benzodiazepine, 7-nitro-2-(3,4-dichlorophenylcarbamoyloxyamino)-5-(2-fluorophenyl)-3H-1,4-benzodiazepine, 7-nitro-2-(2,6-dimethylphenylcarbamoyloxyamino)-5-(2-fluorophenyl)-3H-1,4-benzodiazepine, 7-nitro-2-(3-trifluoromethylphenylcarbamoyloxyamino)-5-(2-fluorophenyl)-3H-1,4-benzodiazepine, 7-nitro-2-(4-chlorophenylcarbamoyloxyamino)-5-(2-fluorophenyl)-3H-1,4-benzodiazepine, 7-nitro-2-(3-chlorophenylcarbamoyloxyamino)-5-(2-pyridyl)-3H-1,4-benzodiazepine, 7-nitro-2-(3-fluorophenylcarbamoyloxyamino)-5-(2-pyridyl)-3H-1,4-benzodiazepine, 7-nitro-2-(3-bromophenylcarbamoyloxyamino)-5-(2-pyridyl)-3H-1,4-benzodiazepine, 7-nitro-2-(3,4-dichlorophenylcarbamoyloxyamino)-5-(2-pyridyl)-3H-1,4-benzodiazepine, 7-nitro-2-(2,6-dimethylphenylcarbamoyloxyamino)-5-(2-pyridyl)-3H-1,4-benzodiazepine, 7-nitro-2-(3-trifluoromethylphenylcarbamoyloxyamino)-5-(2-pyridyl)-3H-1,4-benzodiazepine, 7-nitro-2-(4-chlorophenylcarbamoyloxyamino)-5-(2-pyridyl)-3H-1,4-benzodiazepine, 7-trifluoromethyl-2-(3-chlorophenylcarbamoyloxyamino)-5-(2-chlorophenyl)-3H-1,4-benzodiazepine, 7-trifluoromethyl-2-(3-chlorophenylcarbamoyloxyamino)-5-phenyl-3H-1,4-benzodiazepine, 7-trifluoromethyl-2-(3-chlorophenylcarbamoyloxyamino)-5-(2-fluorophenyl)-3H-1,4-benzodiazepine, 7-trifluoromethyl-2-(3-chlorophenylcarbamoyloxyamino)-5-(2-pyridyl)-3H-1,4-benzodiazepine, 7-chloro-2-(3-chlorophenylcarbamoyloxyamino)-5-(2-trifluoromethylphenyl)-3H-1,4-benzodiazepine, 7-bromo-2-(3-chlorophenylcarbamoyloxyamino)-5-(2-trifluoromethylphenyl)-3H-1,4-benzodiazepine, 7-fluoro-2-(3-chlorophenylcarbamoyloxyamino)-5-(2-trifluoromethylphenyl)-3H-1,4-benzodiazepine, 7-nitro-2-(3-chlorophenylcarbamoyloxyamino)-5-(2-trifluoromethylphenyl)-3H-1,4-benzodiazepine and 7-trifluoromethyl-2-(3-chlorophenylcarbamoyloxyamino)-5-(2-trifluoromethylphenyl)-3H-1,4-benzodiazepine.

In accordance with the process described, the compounds of the formula I can be isolated as such or in the form of an acid addition salt. The salts are preferably the pharmaceutically tolerated, non toxic addition salts with suitable acids, such as, for example, those with inorganic acids, such as hydrochloric acid, hydrobromic acid and hydroiodic acid, nitric acid, sulfuric acid or phosphoric acid, or with organic acids, such as formic acid, acetic acid, propionic acid, succinic acid, tartaric acid, maleic acid, glycolic acid, lactic acid, hydroxymaleic acid, fumaric acid, oxalic acid, citric acid, malic acid, mucic acid, benzoic acid, salicylic acid, aceturic acid, embonic acid, naphthelene-1,5-disulfonic acid, ascorbic acid, phenylacetic acid, p-aminosalicylic acid, hydroxyethanesulfonic acid, benzenesulfonic acid or synthetic resins which contain acid groups, for example those having ion exchange action.

The acid addition salt obtained thereby can be converted into the free compound according to known processes, for example by treatment of the salt with a base, such as a metal hydroxide, metal alcoholate or metal carbonate, with ammonia or with a hydroxyl ion exchanger or with some other suitable reagent. An acid addition salt which is obtained can be converted according to known processes into another salt; thus, for example, a salt of an inorganic acid can be treated with a metal salt of an acid, such as, for example, a sodium, barium or silver salt, in a suitable diluent in which the inorganic salt obtained is insoluble, and can, in this way, be removed from the reaction medium. An acid addition salt can also be converted into another acid addition salt by treatment with an anion-exchanger preparation. A quaternary ammonium salt can be prepared by reaction of the free base with an alkyl halide.

In German Offenlegungsschrift No. 2,533,575, lactam oxime carbamates which have an action on the circulatory system are described, while in German Offenlegungsschriften Nos. 2,005,176 and 2,135,595 and in U.S. Pat. No. 3,857,854, oxyamino-3H-1,4-benzodiazepines are claimed which have an anxiolytic action associated with sedation. It was, however, not to be expected that the carbamoyloxyamino-3H-1,4-benzodiazepines according to the invention, of the general formula I, not yet described, would show such a dramatic split between anxiolysis and sedation. In the therapeutic doses to be employed, practically no sedation occurs.

The compounds according to the invention, and their pharmacologically tolerated salts, are investigated in the rat by the Geller conflict test (punishment discrimination). (Literature on this test: I. Geller et al., Psychopharmacologia, Volume III, pages 374–385 (1962)):

Female Wistar rats weighing 100–120 g are first allowed to learn, in a so-called Skinner box, to press a button for which they are rewarded with milk. After a certain initial learning phase, the frequency of milk reward per unit button-pressing rate is gradually reduced. To this is added a tone phase, in which the reward is coupled with a slight electric shock received by the feet via the cage grid.

After an average of 6–8 weeks' training, most animals have reached the training criterion, namely continual button-pressing in the shock-free phase, with 100–200 pressings in 10 minutes, and reduction of the button-pressing rate, in the shock phase, to 4–5 button pressings in 3 minutes.

The compounds according to the invention are then administered orally ½ an hour before the animals are placed in the Skinner boxes. An increase in the number of button pressings in the shock phase relative to the training values (on the previous day) are considered to be a sign of an anxiolytic action of the test substance, whilst a reduction in the button-pressing rate in the shock-free phase is considered a sign of a sedative action of the preparation. The button-pressing rates under the influence of the preparation are stated in % of the control values; a significance calculation is carried out by means of a non-parametric test, namely the so-called WILCOXON matched pairs signed ranks test (S. SIEGEL, Non Parametric Statistics, pages 75–83). In most cases, a minimum effective dose (MED) is stated.

The compounds according to the invention, administered orally at 10–50 mg/kg, produce a surprisingly great increase in the button-pressing rate in the shock phase, while in the shock-free phase no sedation is observed at up to 100 mg/kg administered orally. Accordingly, the compounds according to the invention are novel anxiolytic agents, with a great split between anxiolytic action and sedative action. The compounds have a low toxicity. The LD$_{50}$ values (for intraperitoneal administration to mice) are in general above 1,000 mg/kg.

The compounds according to the invention and their pharmaceutically tolerated salts are effective over a broad dosage range, the particular dose administered depending on various factors such as, for example, the particular compound used and the condition, type and size of the mammal to be treated. The requisite dose per day for treatment of adult man is normally within the range of 1–60 mg.

For the treatment of test animals, such as mice and rats, individual doses of 5–50 mg per kg are appropriate. The active compounds according to the invention, and their salts, are normally administered orally or by injection.

The medicament used is at least one compound according to the invention or a salt thereof, in combination with a pharmaceutically tolerated carrier suitable for this compound or salt. To prepare the pharmaceutical agents according to the invention, the active ingredient is as a rule mixed with a carrier or diluted with a carrier or enclosed in a carrier which can be in the form of a capsule, in the form of a sachet or in the form of some other container; if the carrier serves as a diluent, it can be a solid, semi-solid or liquid material, which serves as a diluent, auxiliary or medium for the active ingredient (active substance). Examples of suitable carriers are lactose, dextrose, sucrose, sorbitol, mannitol, starch, gum acacia, calcium phosphate, alginates, tragacanth, gelatin, syrup, methylcellulose, methyl hydroxybenzoate, propyl hydroxybenzoate, talc, magnesium stearate or mineral oil.

The pharmaceutical agents according to the invention can be formulated, in a manner known per se, so that after administration to the patients they release the active compound rapidly, continuously or in a retarded manner.

Depending on the route of administration, the pharmaceutical agents mentioned above can be converted to tablets, capsules or suspensions for oral use, or to injection solutions for parenteral use.

EXAMPLE 1

7-Chloro-5-phenyl-2-phenylcarbamoyloxyamino-3H-1,4-benzodiazepine (a) 1.43 g of 7-chloro-2-hydroxyamino-5-phenyl-3H-1,4-benzodiazepine are dissolved in 25 ml of dimethylformamide and 0.6 ml of phenylisocyanate is added to the solution at room temperature. After stirring for 3 hours at room temperature, the reaction solution is poured into 200 ml of ice water, stirred for 30 minutes and filtered off under suction, and the residue is rinsed well with water. After drying in a high vacuum at 40° to 50° C., the colorless substance melts at 212° to 215° C. Yield 1.8 g.

(b) 7.5 g of 7-chloro-1,3-dihydro-5-phenyl-2H-1,4-benzodiazepine-2-thione are suspended in 125 ml of dioxane and 50 ml of dimethylformamide and 2.2 g of sodium bicarbonate and 1.8 g of hydroxylammonium chloride are added to the suspension. After stirring for 8 hours at room temperature (monitoring by thin layer chromatography), the mixture is filtered off under suction and 2.8 ml of phenylisocyanate are added to the filtrate. After stirring for 30 minutes, the reaction mixture is added dropwise into 200 ml of water and the mixture is filtered off under suction. Recrystallization from ethanol/dimethylformamide yields colorless crystals of melting point 215°–217° C. Yield 4.6 g.

EXAMPLE 2

7-Chloro-2-(3-chlorophenylcarbamoyloxyamino)-5-phenyl-3H-1,4-benzodiazepine (a) 1.5 g of 7-chloro-2-hydroxyamino-5-phenyl-3H-1,4-benzodiazepine are initially introduced into 25 ml of dimethylformamide and 0.6 ml of 3-chlorophenyl isocyanate is added to the mixture. After stirring for 2 hours at room temperature (monitoring by thin layer chromatography), the reaction mixture is poured into 200 ml of ice water, stirred for 30 minutes and filtered off under suction. After drying in vacuo, the residue is recrystallized from ethanol.

2.05 g of colorless crystals of melting point 157° to 159° C. The hydrochloride melts at 210° C. (from methanol/dimethylformamide) with decomposition.

(b) 30 g of 7-chloro-1,3-dihydro-5-phenyl-2H-1,4-benzodiazepine-2-thione are suspended in 500 ml of dioxane and 17.6 g of sodium bicarbonate and 7.2 g of hydroxylammonium chloride are then added to the suspension. By addition of dimethylformamide, nearly all material is brought into solution. After stirring for 8 hours at room temperature (monitoring by thin layer chromatography), the mixture is filtered off under suction and 12.8 ml of 3-chlorophenyl isocyanate are added to the filtrate. The mixture is stirred for 1 hour, water is added to it and it is filtered off under suction. Recrystallization from ethanol yields colorless crystals of melting point 158° to 159° C. Yield 17.4 g.

EXAMPLE 3

7-Chloro-2-(4-chlorophenylcarbamoyloxyamino)-5-phenyl-3H-1,4-benzodiazepine 2 g of 7-chloro-2-hydroxyamino-5-phenyl-3H-1,4-benzodiazepine are reacted with 1 g of 4-chlorophenyl isocyanate, analogously to Experiment 1a. Melting point 200° to 203° C. (from methanol); yield 2.1 g.

EXAMPLE 4

7-Chloro-2-(2-trifluoromethylphenylcarbamoyloxyamino)-5-phenyl-3H-1,4-benzodiazepine 2 g of 7-chloro-2-hydroxyamino-5-phenyl-3H-1,4-benzodiazepine are reacted with 1 g of 2-trifluoromethylphenyl isocyanate, analogously to Experiment 1a. Yield: 1.8 g of colorless crystals of melting point 190° C. (from methanol/dimethylformamide).

The following Examples (5 to 15) were prepared analogously to Example 1 (Table 1)

TABLE 1

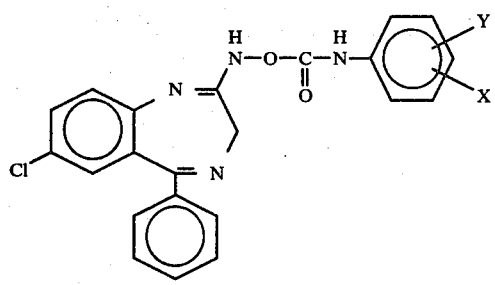

| Examples | X | Y | Melting point (or decomposition point) |
|---|---|---|---|
| 5 | 3-CF$_3$ | H | 95° C. (from ethanol) |

TABLE 1-continued

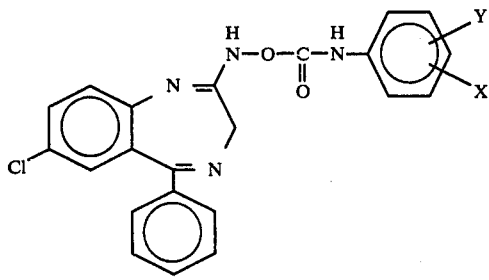

| Examples | X | Y | Melting point (or decomposition point) |
|---|---|---|---|
| 6 | 4-CF₃ | H | 215–218° C. (from isopropanol) |
| 7 | 3-CH₃ | H | 156° C. (from ethanol) |
| 8 | 4-CH₃ | H | 220–221° C. (from ethanol) |
| 9 | 2-F | H | 193–195° C. (from ethanol) |
| 10 | 4-C(CH₃)₃ | H | 221–223° C. (from ethanol) |
| 11 | 3-Cl | 4-CH₃ | 218–220° C. (from methanol) |
| 12 | 2-CH₃ | 6-CH₃ | 198–200° C. (from ethanol) |
| 13 | 3-Cl | 4-Cl | 218–219° C. (from ethanol) |
| 14 | 4-CO₂C₂H₅ | H | 212–214° C. (from ethanol) |
| 15 | 2-CH₃ | 5-CH₃ | 181–183° C. (from ethanol) |

EXAMPLE 16

7-Nitro-5-phenyl-2-phenylcarbamoyloxyamino-3H-1,4-benzodiazepine 3 g of 7-nitro-1,3-dihydro-5-phenyl-2H-1,4-benzodiazepine-2-thione are dissolved in 52 ml of dioxane and 40 ml of dimethylformamide. After addition of 0.9 g of sodium bicarbonate and 0.75 g of hydroxylammonium hydrochloride, the mixture is stirred for 8 hours (monitoring by thin layer chromatography) and filtered off under suction, and 1 ml of phenylisocyanate is added to the filtrate. The mixture is stirred for 1 hour and poured into water, and the precipitated oil is separated off; ethanol is added to the oil and the crystalline precipitate is filtered off under suction.

Yield: 1 g of slightly yellow crystals of melting point 182° to 185° C. (with decomposition).

EXAMPLE 17

2-(3-Chlorophenylcarbamoyloxyamino)-7-nitro-5-phenyl-3H-1,4-benzodiazepine 3 g of 7-nitro-1,3-dihydro-5-phenyl-2H-1,4-benzodiazepine-2-thione are reacted with 3-chlorophenyl isocyanate and worked up, analogously to Example 16. After purification by column chromatography, 0.6 g of yellow crystals of melting point 123° to 125° C. (from ethanol) are produced.

EXAMPLE 18

5-(2-Chlorophenyl)-7-nitro-2-phenylcarbamoyloxyamino-3H-1,4-benzodiazepine 2 g of 5-(2-chlorophenyl)-7-nitro-1,3-dihydro-2H-1,4-benzodiazepine-2-thione are reacted with 0.8 g of sodium bicarbonate and 0.7 g of hydroxylammonium chloride, analogously to Example 16. After stirring for 8 hours at room temperature, 0.8 ml of phenyl isocyanate are added, and the mixture is stirred for ½ an hour and precipitated with water; the oil produced is crystallized by means of ethanol. Recrystallization from ethanol yields 2 g of yellow crystals of melting point 201° to 203° C.

EXAMPLE 19

5-(2-Chlorophenyl)-2-(3-chlorophenylcarbamoyloxyamino)-7-nitro-3H-1,4-benzodiazepine 2 g of 5-(2-chlorophenyl)-7-nitro-1,3-dihydro-2H-1,4-benzodiazepine-2-thione are reacted with 0.8 ml of 3-chlorophenyl isocyanate, analogously to Example 18, and worked up as described therein. Yield: 0.6 g of yellow crystals of melting point 130° to 135° C. (from ethanol).

EXAMPLE 20

7-Bromo-2-phenylcarbamoyloxyamino-5-(2-pyridyl)-3H-1,4-benzodiazepine 1 g of sodium bicarbonate and 0.8 g of hydroxylammonium chloride are added to 3 g of 7-bromo-5-(2-pyridyl)-1,3-dihydro-2H-1,4-benzodiazepine-2-thione in 60 ml of dioxane containing dimethylformamide and the mixture is stirred for 8 hours. 0.3 g of sodium bicarbonate and 0.25 g of hydroxylammonium chloride are again added and the mixture is stirred for 30 minutes at 50° C. The mixture is filtered off under suction when cold, and 1.0 ml of phenylisocyanate is added to the filtrate which is stirred for 1 hour. After the usual working up process, 1.6 g of colorless crystals are precipitated and are recrystallized from ethanol. Melting point 190° to 192° C.

EXAMPLE 21

7-Bromo-2-(3-chlorophenylcarbamoyloxyamino)-5-(2-pyridyl)-3H-1,4-benzodiazepine is prepared from 3 g of 7-bromo-5-(2-(pyridyl)-1,3-dihydro-2H-1,4-benzodiazepine-2-thione and finally 1.1 ml of 3-chlorophenyl isocyanate, analogously to Example 20. Yield: 1.6 g, melting point: 190° to 191° C.

EXAMPLE 22

7-Chloro-5-(2-fluorophenyl)-2-phenylcarbamoyloxyamino-3H-1,4-benzodiazepine 0.6 g of sodium bicarbonate and 0.5 g of hydroxylammonium chloride are added to 2 g of 7-chloro-5-(2-fluorophenyl)-1,3-dihydro-2H-1,4-benzodiazepine-2-thione in 40 ml of dioxane and 20 ml of dimethylformamide and the mixture is stirred for 8 hours at room temperature. Further addition of 0.2 g of sodium bicarbonate and 0.2 g of hydroxylammonium chloride, stirring for ½ hour at 50° C. and addition of 0.8 ml of phenylisocyanate yields, after the usual working up process, 0.7 g of colorless crystals of melting point 126° to 128° C. (from isopropanol).

Examples 23 to 25 may be prepared analogously to Example 22

EXAMPLE 23

7-Chloro-2-(3-chlorophenylcarbamoyloxyamino)-5-(2-fluorophenyl)-2H-1,4-benzodiazepine Melting point 194° to 196° C. (from ethanol).

EXAMPLE 24

7-Chloro-2-(3-chlorophenylcarbamoyloxyamino)-5-(2-chlorophenyl)-2H-1,4-benzodiazepine Melting point 125° to 137° C. (from ethanol).

EXAMPLE 25

7-Chloro-5-(2-chlorophenyl)-2-phenylcarbamoyloxyamino-2H-1,4-benzodiazepine

Melting point 224° to 226° C. (from ethanol).

EXAMPLE 26

(+)-5-(2-Chlorophenyl)-2-(3-chlorophenylcarbamoyloxyamino)-3-methyl-7-nitro-3H-1,4-benzodiazepine 1.5 g of (+)-5-(2-chlorophenyl)-1,3-dihydro-3-methyl-7-nitro-2H-1,4-benzodiazepine-2-thione, prepared according to German Offenlegungsschrift No. 2,546,612, are suspended in 50 ml of dioxane, 0.5 g of sodium bicarbonate and 0.4 g of hydroxylammonium hydrochloride are added and the mixture is stirred for 8 hours at room temperature (monitoring by thin layer chromatography). The mixture is filtered off under suction and 0.5 ml of 3-chlorophenyl isocyanate is added to the filtrate, which is stirred for 1 hour. After addition of water, the precipitate is filtered off under suction.

Yield: 0.8 g of slightly yellow crystals of melting point 137° to 139° C.

EXAMPLE 27

7-Chloro-3-dimethylcarbamoyloxy-5-phenyl-2-phenylcarbamoyloxyamino-3H-1,4-benzodiazepine (a) 7-Chloro-1,3-dihyydro-5-phenyl-3-phenyloxycarbonyloxy-2H-1,4-benzodiazepine-2-thione 1 g of 7-chloro-1,3-dihydro-5-phenyl-3-phenyloxycarbonyloxy-2H-1,4-benzodiazepin-2-one (prepared from oxazepam according to German Offenlegungsschrift No. 2,142,181) is suspended in 20 ml of dioxane, 0.5 g of dimeric p-methoxyphenyl-thionophosphine sulfide (according to S. O. Lawesson) is added and the mixture is stirred for 3 hours at 80° C. (monitoring by thin layer chromatography). After the mixture becomes cold it is poured into ice water and filtered off under suction. Yield 1.5 g of melting point 113° C. (decomposition).

(b) 7-Chloro-5-phenyl-2-phenylcarbamoyloxyamino-3-phenyloxycarbonyloxy-3H-1,4-benzodiazepine 4 g of 7-chloro-1,3-dihydro-5-phenyl-3-phenyloxycarbonyloxy-2H-1,4-benzodiazepine-2-thione are suspended in 90 ml of dioxane and 1.7 g of sodium bicarbonate and 1.3 g of hydroxylammonium chloride are added, and the mixture is stirred for 8 hours at room temperature (monitoring by thin layer chromatography). After addition of 0.9 ml of phenylisocyanate, the mixture is stirred for 1 hour and water is added to it. The oil produced is decanted off and stirred up with ethanol, and the slurry of crystals is filtered off under suction.

Yield: 0.5 g of melting point 124° to 128° C. (decomposition).

(c) 7-Chloro-3-dimethylcarbamoyloxy-5-phenyl-2-phenylcarbamoyloxyamino-3H-1,4-benzodiazepine 5 ml of a solution of dimethylamine in methanol (content 30 g of dimethylamine in 100 ml) are added to 0.5 g of 7-chloro-5-phenyl-2-phenylcarbamoyloxyamino-3-phenyloxycarbonyloxy-3H-1,4-benzodiazepine in 10 ml of methanol, whilst stirring. The mixture is stirred for 5 hours at room temperature and water is added to it; the residue is filtered off and dried.

Yield: 0.2 g of yellowish crystals of melting point from 99° C., decomposition.

Examples 28 to 30 may be prepared analogously to Example 27:

EXAMPLE 28

7-Chloro-2-(3-chlorophenylcarbamoyloxyamino)-3-dimethylcarbamoyloxy-5-phenyl-3H-1,4-benzodiazepine Melting point 105° C. (decomposition).

EXAMPLE 29

7-Chloro-5-(2-chlorophenyl)-2-(3-chlorophenylcarbamoyloxyamino)-3-dimethylcarbamoyloxy-3H-1,4-benzodiazepine Melting point 121° C. (decomposition).

EXAMPLE 30

7-Chloro-5-(2-chlorophenyl)-3-dimethylcarbamoyloxy-2-phenylcarbamoyloxyamino-3H-1,4-benzodiazepine Melting point 117° C. (decomposition).

EXAMPLE 31

2-(3,4-Dichlorophenylcarbamoyloxyamino)-5-(2-chlorophenyl)-7-nitro-3H-1,4-benzodiazepine 1 g of 5-(2-chlorophenyl)-2-hydroxyamino-7-nitro-3H-1,4-benzodiazepine of Example 18 is reacted with 0.56 g of 3,4-dichlorophenyl isocyanate and worked up as in Example 18. Yield: 1.1 g, melting point: 190° to 192° C. decomposition (from ethanol).

EXAMPLE 32

2-(3-Chlorophenylcarbamoyloxyamino)-5-(2-fluorophenyl)-7-nitro-3H-1,4-benzodiazepine 2.5 g of 1,3-dihydro-5-(2-fluorophenyl)-7-nitro-2H-1,4-benzodiazepine-2-thione are dissolved in 65 ml of dioxane and 30 ml of dimethylformamide, and 1.0 g of sodium bicarbonate and 0.88 g of hydroxylammonium chloride are added to the solution. After stirring for 2 hours at room temperature, more sodium bicarbonate and hydroxylammonium chloride are added. After yet another 2 hours, the mixture is filtered off under suction and 0.58 ml of 3-chlorophenyl isocyanate is added. The mixture is worked up analogously to Example 18.

Yield: 0.55 g, melting point: 126° to 130° C. (from methanol/ethanol).

We claim:

1. A carbamoyloxyamino-1,4-benzodiazepine of the formula

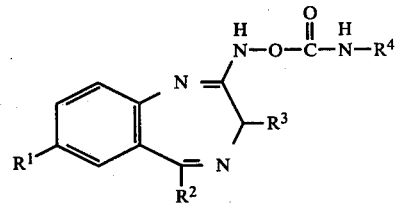

or of the formula

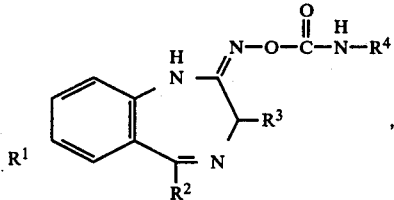

or a physiologically tolerated salt of such a compound, wherein $R^1$ is halogen, nitro, or trifluoromethyl;

$R^2$ is phenyl, pyridyl, or phenyl which is mono- or di-substituted by $C_1$–$C_4$ alkyl, $C_1$–$C_4$ alkoxy, hydroxy, halogen, or trifluoromethyl;

$R^3$ is hydrogen, $C_1$–$C_4$ alkyl, monoalkylcarbamoyloxy, or dialkylcarbamoyloxy; and $R^4$ is phenyl or phenyl which is mono- or di-substituted by halogen, nitro, cyano, trifluoromethyl, $C_1$–$C_4$ alkyl, $C_1$–$C_4$ alkoxy, hydroxy, or dialkylamino having 1–4 carbon atoms in each alkyl.

2. 7-Chloro-2-(3-chlorophenylcarbamoyloxyamino)-5-phenyl-3H-1,4-benzodiazepine.

3. 5-(2-Chlorophenyl)-2-(3-chlorophenylcarbamoyloxyamino)-7-nitro-3H-1,4-benzodiazepine.

4. 7-Chloro-5-(2-chlorophenyl)-2-(3-chlorophenylcarbamoyloxyamino)-3H-1,4-benzodiazepine.

5. 2-(3-Chlorophenylcarbamoyloxyamino)-5-(2-fluorophenyl)-7-nitro-3H-1,4-benzodiazepine.

6. 2-(3-Chlorophenylcarbamoyloxyamino)-7-nitro-5-phenyl-3H-1,4-benzodiazepine.

7. 7-Chloro-2-(3-chlorophenylcarbamoyloxyamino)-5-(2-fluorophenyl)-3H-1,4-benzodiazepine.

8. A pharmaceutical preparation for the treatment of anxiety states comprising an anxiolytic amount of a compound as in claim 1 and a pharmaceutically acceptable carrier therefor.

9. A method for treating anxiety states in a patient in need of such treatment, which method comprises orally or parenterally administering to said patient an anxiolytic amount of a compound as in claim 1.

* * * * *